United States Patent
Li et al.

(10) Patent No.: US 10,775,320 B2
(45) Date of Patent: Sep. 15, 2020

(54) AFTERGLOW DETECTION DEVICE AND AFTERGLOW DETECTION METHOD

(71) Applicant: NUCTECH COMPANY LIMITED, Beijing (CN)

(72) Inventors: Shuwei Li, Beijing (CN); Wenjian Zhang, Beijing (CN); Xiang Zou, Beijing (CN); Bozhen Zhao, Beijing (CN); Qingjun Zhang, Beijing (CN); Huishao He, Beijing (CN); Yongqiang Wang, Beijing (CN); Yanchun Wang, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 16/403,555

(22) Filed: May 5, 2019

(65) Prior Publication Data

US 2019/0346380 A1    Nov. 14, 2019

(30) Foreign Application Priority Data

May 9, 2018    (CN) .......................... 2018 1 0437201

(51) Int. Cl.
*A61B 6/00* (2006.01)
*G01N 23/04* (2018.01)
*G01T 1/20* (2006.01)

(52) U.S. Cl.
CPC ........... *G01N 23/04* (2013.01); *A61B 6/4258* (2013.01); *G01T 1/20* (2013.01)

(58) Field of Classification Search
None
See application file for complete search history.

(56) References Cited

U.S. PATENT DOCUMENTS

| 2010/0268074 | A1* | 10/2010 | Van Loef | G01T 1/2018 600/431 |
| 2016/0024380 | A1* | 1/2016 | Ronda | A61B 6/03 250/483.1 |
| 2019/0046151 | A1* | 2/2019 | Tsuyuki | A61B 6/405 |

* cited by examiner

*Primary Examiner* — Hoon K Song
(74) *Attorney, Agent, or Firm* — Kilpatrick Townsend & Stockton, LLP

(57) ABSTRACT

The present disclosure discloses an afterglow detection device and an afterglow detection method. The afterglow detection device comprises: an X-ray tube for emitting an X-ray beam; a first reading circuit for receiving a first detected signal from a to-be-detected detector to form and output a first measurement signal according to the first detected signal, the to-be-detected detector being connected to the first reading circuit and disposed on a beam-out side of the X-ray tube to receive radiation of the X-ray beam and outputting the first detected signal to the first reading circuit at the time of detection; a residual ray detector disposed on a beam-out side of the X-ray tube; a second reading circuit connected to the residual ray detector for receiving a second detected signal from the residual ray detector to form and output a second measurement signal according to the second detected signal.

8 Claims, 5 Drawing Sheets

AFTERGLOW DETECTION DEVICE AND AFTERGLOW DETECTION METHOD

RELATED APPLICATION

The present application claims priority from Chinese application number CN 201810437201.6 filed May 9, 2018, which is herein incorporated by reference.

FIELD

The present disclosure relates to the field of radiation inspection technology, in particular to an afterglow detection device and an afterglow detection method.

BACKGROUND

Afterglow means that a scintillation detector still emits visible light for a period of time after disappearance of an eternal excitation signal (such as a ray beam or visible light or the like) to the scintillation detector. The intensity of the afterglow approximately decreases exponentially with time.

Afterglow is generally measured by a relative intensity after the external excitation signal has disappeared for a period of time. For example, for a typical cesium iodide (thallium) (CsI (TI)) scintillation detector, the output signal of the scintillation detector is unit 1 in the presence of an external excitation signal (such as an X-ray beam). The output signal of the scintillation detector is about 5000 ppm at the moment of 10 ms after disappearance of the excitation signal, that is, the afterglow value of the scintillation detector is about 0.5% at the moment of 10 ms after disappearance of the excitation signal. Even if the scintillation detectors are of the same type, the afterglow values of the scintillation detectors produced by different manufacturers are greatly different, and different detection units have their respective afterglow values.

In an inspection system using a continuous beam-out X-ray source or an isotope radiation source, the afterglow of a scintillator of a scintillation detector is an important factor affecting the final performance index. When the substance to be detected is thick, the intensity of rays from the radiation source is attenuated to less than one thousandth, but the afterglow value may be several times of the intensity value of the attenuated rays, and the afterglow values of different detection units are different, resulting in uneven brightness of images and causing a false signal.

FIG. 1 is a scanned image formed according to a detection signal of a CsI (TI) detector. As can be seen from FIG. 1, at the same steel plate thickness, the right side is brighter than the left side, and different detectors have different afterglow values, resulting in that the image has stripes with different brightness.

FIG. 2 is a scanned image formed according to a detection signal of a cadmium tungstate detector. This scanned image is cleaner than the scanned image described in FIG. 1. Cadmium tungstate is a material with excellent scintillation performance for a scintillation detector, the afterglow time is short and the afterglow value is low.

FIG. 3 is a comparison diagram of the output relative intensity curve (thin solid line) of the CsI (TI) detector before and after disappearance of the excitation signal and the output relative intensity curve (thick solid line) of the cadmium tungstate detector. FIG. 3 represents an afterglow comparison result of a high-afterglow detector represented by a CsI (TI) detector and a low-afterglow detector represented by a cadmium tungstate detector. In FIG. 3, from −10 ms to 0 ms, an X-ray beam as an excitation signal is irradiated to the CsI (TI) detector and the cadmium tungstate detector. After the moment of 0 ms, no X-ray beam is irradiated to the CsI (TI) detector and the cadmium tungstate detector. Therefore, values of the output relative intensity curves of the CsI (TI) detector and the cadmium tungstate detector after the moment of 0 ms represent their respective afterglow values.

There are mainly two methods for solving the problem of uneven brightness of images caused by an afterglow phenomenon.

In one method, a scintillation material with low afterglow is used as the sensitive volume of the scintillation detector, but such scintillation materials are generally low in sensitivity and high in price.

In another method, the output signal of the scintillation detector is corrected for the afterglow of the scintillation detector. In this method, the afterglow of the scintillation detector needs to be measured at first, and then the effect of the afterglow is deducted from the detection result of the scintillation detector according to an algorithm routine, thereby improving the performance of the scintillation detector.

When the afterglow of the scintillation detector is measured, it is necessary to measure afterglow values of some time periods (such as 1 ms, 5 ms and 10 ms) after the X-ray (or gamma ray) is completely turned off. In order to measure the afterglow of the scintillation detector, it is necessary to provide an afterglow detection device and an afterglow detection method which are reliable, easy to use and low in cost.

In general afterglow detection methods a radiation source irradiates the scintillation detector to perform data acquisition of the scintillation detector. After the ray beam is turned off, the data acquisition of the detector is continued for a certain period of time to obtain afterglow data of the detector. The radiation source may be an electron accelerator, an isotope source, an X-ray tube, etc.

Electronic accelerators are expensive, consume a lot of power, and are difficult to popularize. The isotope source always has a gamma-ray beam, and thus has a safety problem. The X-ray tube is small in volume and easy to use, and has an energy range from tens of kilovolts to hundreds of kilovolts. The X-ray tube is generally a continuous beam-out X-ray source, and has certain advantages if it is used as a radiation source for afterglow detection.

However, when an X-ray tube is used as the radiation source for afterglow detection, after the power supply for the X-ray tube is turned off, the X-ray tube still emits X-rays, namely, residual X-rays, and the residual X-rays have an adverse effect on the afterglow detection. Both the intensity of the residual X-rays and the average energy of X-ray photons decrease with time and approximately attenuate exponentially with time. X-ray tubes of different models have different intensities of residual X-rays. Intensity of residual X-rays of a typical X-ray tube at the moment of 10 ms after the power supply is turned off can be 40% of the intensity of the X-rays when the power supply for the X-ray tube is turned on, and the average energy of the X-ray photons attenuates to about 50% of that when the power supply for the X-ray tube is turned on (X-ray tubes from different manufacturers and of different models are greatly different).

In order to reduce the adverse effect of the residual X-rays of the X-ray tube on the afterglow detection, in the related art known to the inventors, when the X-ray tube is used as the radiation source to perform the afterglow detection, it is usually necessary to configure a matched heavy metal block. When a power supply for the X-ray tube is turned off, the heavy metal block is quickly moved to a position between the X-ray tube and the to-be-detected detector to block the residual X-rays, so that the afterglow test results are protected from the effect of the residual X-rays. In order to block the residual X-rays in time, the heavy metal block needs to move at a high speed and to be stationary as soon as possible, so that the heavy metal block needs to have a large accelerated speed, and a set of relatively complicated and costly control system and mechanical system for adjusting the position of the heavy metal block is needed. At present, as the heavy metal block needs to be configured, using the X-ray tube to detect the afterglow of the scintillation detector is only used in laboratories or production workshops, but is difficult to use on product application sites.

SUMMARY

An objective of the present disclosure is to achieve simple and reliable afterglow detection device and afterglow detection method by using an X-ray tube as a radiation source.

In a first aspect of the present disclosure, an afterglow detection device is provided, comprising: an X-ray tube for emitting an X-ray beam; a first reading circuit for receiving a first detected signal from a to-be-detected detector to form and output a first measurement signal according to the first detected signal, the to-be-detected detector being connected to the first reading circuit and disposed on a beam-out side of the X-ray tube to receive radiation of the X-ray beam and outputting the first detected signal to the first reading circuit at the time of detection; a residual ray detector disposed on a beam-out side of the X-ray tube; a second reading circuit connected to the residual ray detector for receiving a second detected signal from the residual ray detector to form and output a second measurement signal according to the second detected signal, the residual ray detector receiving radiation of the X-ray beam and outputting a second detected signal to the second reading circuit; and a computing device in signal connection with the first reading circuit and the second reading circuit to receive the first measurement signal and the second measurement signal, the computing device being configured to compute and output the afterglow detection signal according to the first measurement signal and the second measurement signal after a power supply for the X-ray tube is turned off.

In some embodiments, the computing device is configured to subtract the value of the second measurement signal at a moment after the power supply for the X-ray tube is turned off from the value of the first measurement signal at that moment to serve as the value of the afterglow detection signal at that moment; or the computing device is configured to subtract a corrected value of the second measurement signal at a moment after the power supply for the X-ray tube is turned off from the value of the first measurement signal at that moment to serve as the value of the afterglow detection signal at that moment.

In some embodiments, the output relative intensity of the residual ray detector at the moment of 10 ms after disappearance of an excitation signal is lower than 0.05% of the output relative intensity in the presence of the excitation signal.

In some embodiments, the residual ray detector comprises a cadmium tungstate detector.

In some embodiments, the afterglow detection device comprises a heavy metal sheet disposed on a beam-out side of the X-ray tube and located between the X-ray tube and the to-be-detected detector and between the X-ray tube and the residual ray detector, so as to attenuate the intensity of the X-ray beam.

In a second aspect of the present disclosure, an afterglow detection method for detecting afterglow of a scintillation detector by using the afterglow detection device according to any one of the first aspect of the present disclosure is provided, comprising: turning on a power supply for the X-ray tube to emit an X-ray beam by the X-ray tube, and turning off the power supply for the X-ray tube after a period of time; receiving radiation of the X-ray beam, and outputting a first detected signal by the to-be-detected detector; receiving the first detected signal, and forming and outputting a first measurement signal according to the first detected signal by the first reading circuit; receiving radiation of the X-ray beam, and outputting a second detected signal by the residual ray detector; receiving the second detected signal, and forming and outputting a second measurement signal according to the second detected signal the second reading circuit; receiving the first measurement signal and the second measurement signal, and computing and outputting an afterglow detection signal according to the first measurement signal and the second measurement signal by the computing device after the power supply for the X-ray tube is turned off.

In some embodiments, the computing device subtracts the value of the second measurement signal at a moment after the power supply for the X-ray tube is turned off from the value of the first measurement signal at that moment to serve as the value of the afterglow detection signal at that moment; or the computing device subtracts the corrected value of the second measurement signal at a moment after the power supply for the X-ray tube is turned off from the value of the first measurement signal at that moment to serve as the value of the afterglow detection signal at that moment.

In some embodiments, the first measurement signal is an output relative intensity of the to-be-detected detector, and the second measurement signal is an output relative intensity of the residual ray detector.

Based on the afterglow detection device and the afterglow detection method provided by the present disclosure, the X-ray tube is used as a radiation source, the residual ray detector is used to detect the intensity of the residual X-ray beam after the power supply for the X-ray tube is turned off, and a relatively accurate afterglow detection signal of the to-be-detected detector 10 is obtained by deducting the effect of the second measurement signal derived from the residual ray detector and related to the residual X-ray beam from the first measurement signal derived from the to-be-detected detector 10. The afterglow detection device and the afterglow detection method are simple and reliable. Since it is not necessary to provide a heavy metal block for blocking the residual X-ray beam after the power supply for the X-ray tube is turned off, the detection device and the detection method can be used on X-ray inspection equipment sites.

Other features and advantages of the present disclosure will become clear from the following detailed description of exemplary embodiments of the present disclosure with reference to the drawings.

BRIEF DESCRIPTION OF THE DRAWINGS

The drawings illustrated herein are intended to provide a further understanding of the present disclosure, and constitute a part of the present application. Exemplary embodiments of the present disclosure and illustration thereof are intended to interpret the present disclosure, rather than forming improper limitation to the present disclosure. In the drawings.

DETAILED DESCRIPTION OF THE EMBODIMENTS

Figure 1:
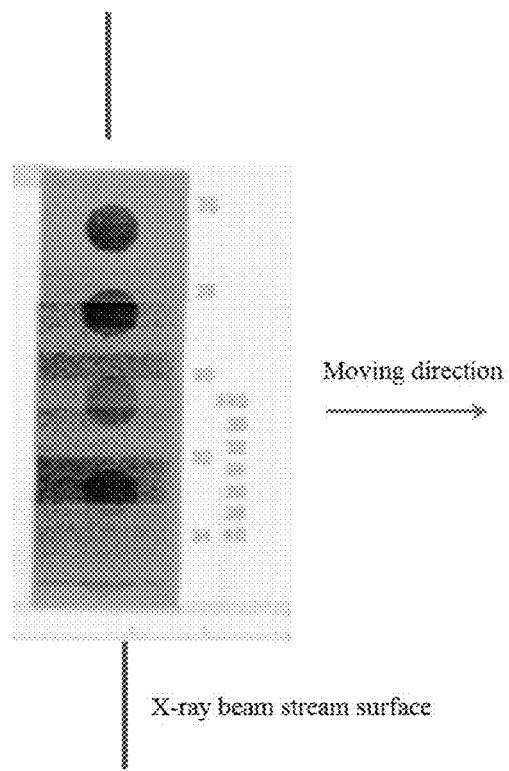
FIG. 1 is a scanned image obtained according to a detection signal from a CsI (TI) detector.
Figure 2:
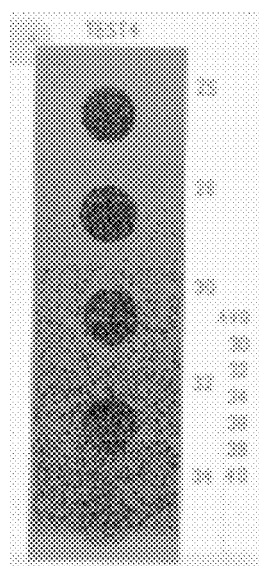
FIG. 2 is a scanned image obtained according to a detection signal from a cadmium tungstate detector.
Figure 3:
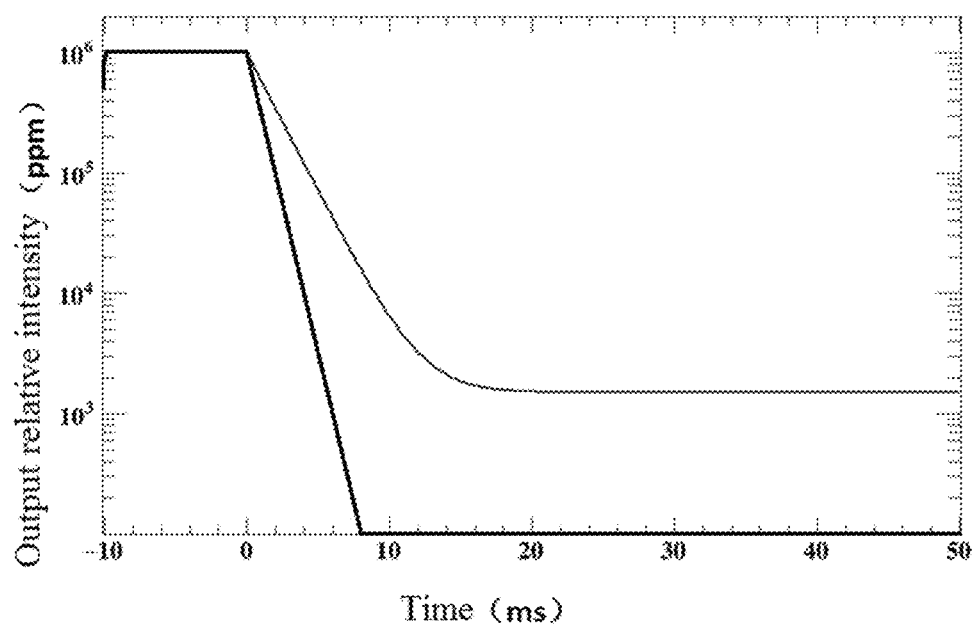
FIG. 3 is a comparison diagram of the output relative intensity curve (thin solid line) of the CsI (TI) detector before and after disappearance of an excitation signal and the output relative intensity curve (thick solid line) of the cadmium tungstate detector.

The technical solutions in the embodiments of the present disclosure will be clearly and completely described below in conjunction with accompanying drawings in the embodiments of the present disclosure. It is obvious that the described embodiments are merely a part of, instead of all the embodiments of the present disclosure. The following description of the at least one exemplary embodiment is merely illustrative, and will never serve as any limitation to the present disclosure and application or use thereof. All other embodiments obtained by the person of ordinary skill in the art based on the embodiments of the present disclosure without creative efforts are within the protection scope of the present disclosure.

Unless otherwise stated specifically, the relative arrangement of the components and steps, numerical expressions and numerical values set forth in these embodiments are not intended to limit the scope of the present disclosure. In addition, it should be understood that the dimensions of various parts shown in the drawings are not actually scaled for the convenience of description. Techniques, methods and equipment known to the person of ordinary skill in relevant arts may not be discussed in detail, but should be considered as part of the granted description where appropriate. In all of the examples shown and discussed herein, any specific values should be construed as illustrative only but not as limitations. Accordingly, other examples of the exemplary embodiments may have different values. It should be noted that similar reference signs and letters indicate similar items in the following figures, and therefore, once an item is defined in one figure, it does not need to be further discussed in subsequent figures.

In the description of the present disclosure, it should be understood that using terms "first", "second" and the like to define components and parts is merely for the purpose of facilitating distinguishing corresponding components and parts. The terms above have no special meanings unless otherwise stated, and thus cannot be construed as limiting the protection scope of the present disclosure.

Figure 4:
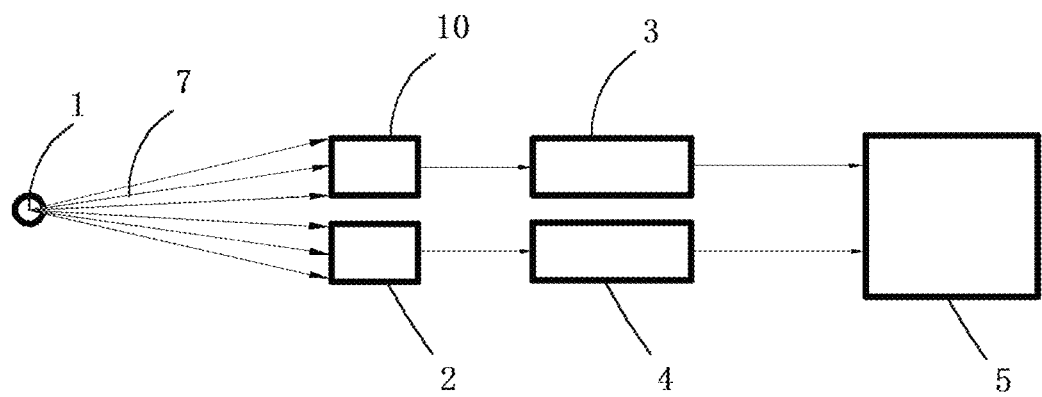
FIG. 4 is a principle diagram of an afterglow detection device according to an embodiment of the present disclosure.

FIG. 4 shows a principle diagram of an afterglow detection device of an embodiment of the present disclosure. As shown in FIG. 4, the afterglow detection device of the embodiment of the present disclosure comprises an X-ray tube 1, a first reading circuit 3, a residual ray detector 2, a second reading circuit 4, and a computing device 5.

The X-ray tube 1 is configured to emit an X-ray beam. The first reading circuit 3 is configured to be connected to the to-be-detected detector 10. The to-be-detected detector 10 is disposed on a beam-out side of the X-ray tube 1 at the time of detection to receive radiation of the X-ray beam, and outputs a first detected signal to the first reading circuit 3. The first reading circuit 3 forms and outputs a first measurement signal according to the first detected signal. The residual ray detector 2 is disposed on the beam-out side of the X-ray tube 1. The second reading circuit 4 is connected to the residual ray detector 2. The residual ray detector 2 receives radiation of the X-ray beam and outputs a second detected signal to the second reading circuit 4. The second reading circuit 4 forms and outputs a second measurement signal according to the second detected signal. The computing device 5 is in signal connection with the first reading circuit 3 and the second reading circuit 4. The computing device 5 receives the first measurement signal and the second measurement signal, and computes and outputs an afterglow detection signal according to the first measurement signal and the second measurement signal after the power supply for the X-ray tube 1 is turned off.

In the embodiment of the present disclosure, the X-ray tube 1 is used as a radiation source, a residual ray detector is used to detect the intensity of a residual X-ray beam after the power supply for the X-ray tube is turned off. A relatively accurate afterglow detection signal of the to-be-detected detector 10 is obtained by deducting the effect of the second measurement signal derived from the residual ray detector and related to the residual X-ray beam from the first measurement signal derived from the to-be-detected detector 10. The afterglow detection device is simple and reliable. Since it is not necessary to provide a heavy metal block for blocking the residual X-ray beam after the power supply for the X-ray tube is turned off, the detection device can be used on X-ray inspection equipment sites.

In this embodiment, the residual ray detector 2 has an afterglow value at the moment of 10 ms after disappearance of the excitation signal lower than 0.05% of the afterglow value in the presence of the excitation signal. The residual ray detector 2 may comprise, for example, a cadmium tungstate detector. The afterglow of the residual ray detector 2 that meets this requirement is about one orders of magnitude or more lower than the afterglow of the conventional to-be-detected detector 10 (such as a CsI (TI) detector). In the case, the second measurement signal may be directly subtracted from the first measurement signal to obtain a relatively accurate afterglow detection result.

In this embodiment, the computing device 5 subtracts the value of the second measurement signal at a moment after the power supply for the X-ray tube 1 is turned off from the value of the first measurement signal at that moment to serve as the value of the afterglow detection signal at that moment. In this embodiment, the first measurement signal is an output relative intensity of the to-be-detected detector 10, and the second measurement signal is an output relative intensity of the residual ray detector 2.

In some embodiments, the computing device 5 may also subtract the corrected value of the second measurement signal at a moment after the power of the X-ray tube 1 is turned off from the value of the first measurement signal at that moment to serve as the value of the afterglow detection signal at that moment.

For example, the corrected value of the second measurement signal may be the product of a value of the second measurement signal and a correction coefficient. For another example, the corrected value of the second measurement signal is a difference between the value of the second measurement signal and a correction parameter. For example, if the afterglow value of the residual ray detector 2 is not low enough, the effect due to the afterglow value of the residual ray detector 2 in the second measurement signal and other situations may be removed from the second measurement signal by obtaining the corrected value at first.

This embodiment also provides an afterglow detection method for detecting afterglow of a scintillation detector by using the aforementioned afterglow detection device. The afterglow detection method comprises: turning on a power supply for the X-ray tube 1 to emit an X-ray beam by the X-ray tube 1, and turning off the power supply for the X-ray tube 1 after a period of time; receiving radiation of the X-ray beam of the X-ray tube 1 and outputting a first detected signal by the to-be-detected detector 10; receiving the first detected signal and forming and outputting a first measurement signal according to the first detected signal by the first reading circuit 3; receiving radiation of the X-ray beam of the X-ray tube 1 and outputting a second detected signal by the residual ray detector 2; receiving the second detected signal, and forming and outputting a second measurement signal according to the second detected signal by the second reading circuit 4; receiving the first measurement signal and the second measurement signal, and computing and outputting an afterglow detection signal of the to-be-detected detector 10 according to the first measurement signal and the second measurement signal by the computing device after the power supply for the X-ray tube 1 is turned off.

The afterglow detection method has the same advantages as the afterglow detection device.

In this embodiment, the value of the second measurement signal at a moment after the power supply for the X-ray tube 1 is turned off may be subtracted from the value of the first measurement signal at that moment to serve as the value of the afterglow detection signal at that moment. In this embodiment, the first measurement signal is an output relative intensity of the to-be-detected detector 10, and the second measurement signal is an output relative intensity of the residual ray detector 2.

In some embodiments, the corrected value of the second measurement signal at a moment after the power supply for the X-ray tube 1 is turned off may be subtracted from the value of the first measurement signal at that moment to serve as the value of the afterglow detection signal at that moment. For example, the corrected value of the second measurement signal may be a product of the value of the second measurement signal and a correction coefficient. For another example, the corrected value of the second measurement signal may also be a difference between the value of the second measurement signal and a correction parameter.

In this embodiment, a scintillation detector serving as the to-be-detected detector 10 is connected to the first reading circuit 3 before the beginning of the afterglow detection. Meanwhile, as shown in FIG. 4, the residual ray detector 2 is connected to the second reading circuit 4, and both the first reading circuit 3 and the second reading circuit 4 are connected to the computing device 5. Both the to-be-detected detector 10 and the residual ray detector 2 are located on the beam-out side of the X-ray tube 1. At the beginning of the detection, the power supply for the X-ray tube 1 is turned on, and the X-ray beam 7 is emitted from a target spot of the X-ray tube 1 and radiated to the to-be-detected detector 10 and the residual ray detector 2. The first reading circuit 3 performs data acquisition on the first detected signal output by the to-be-detected detector 10, and the second reading circuit 4 performs data acquisition on the second detected signal output by the residual ray detector 2. After a period of time (for example, 10 ms), the power supply for the X-ray tube 1 is turned off, the X-ray tube 1 continues to emit the residual X-ray beam, and the to-be-detected detector 10 and the residual ray detector 2 continue to detect the intensity of the residual X-ray beam emitted by the X-ray tube 1.

In this embodiment, the first detected signal output by the to-be-detected detector 10 forms an output relative intensity as the first measurement signal by means of the first reading circuit 3, and the second detected signal output by the residual ray detector 2 forms an output relative intensity as the second measurement signal by means of the second reading circuit 4. After receiving the first measurement signal and the second measurement signal, the computing device 5 subtracts the value of the second measurement signal from the value of the first measurement signal after the power supply for the X-ray tube 1 is turned off, thereby obtaining the value of the afterglow detection signal. The value of the afterglow detection signal is a relative intensity representing magnitude of the afterglow.

Figure 5:
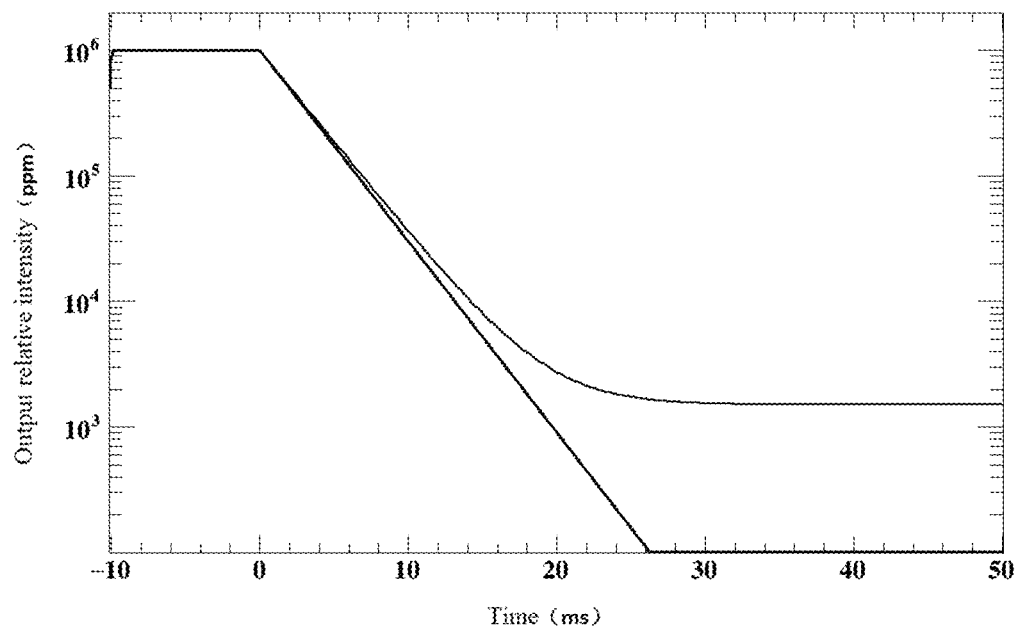
FIG. 5 is a schematic diagram of the output relative intensity curve (thin solid line) of the to-be-detected detector when the afterglow detection device of the embodiment as shown in FIG. 4 detects the afterglow and the output relative intensity curve (thick solid line) of the residual ray detector.

FIG. 5 shows a schematic diagram of the output relative intensity curve (thin solid line) of the to-be-detected detector in the afterglow detection device of the embodiment shown in FIG. 4 and the output relative intensity curve (thick solid line) of the residual ray detector. As shown in FIG. 5, the output relative intensity curve of the residual ray detector 2 represents the intensity change of the X-ray beam before and after the power supply for the X-ray tube 1 is turned off. After the power supply for the X-ray tube 1 is turned off, the afterglow values of the to-be-detected detector 10 at each time point is obtained by deducting the output relative intensity curve of the residual ray detector 2 from the output relative intensity curve of the to-be-detected detector 10 at each time point.

Both the first reading circuit 3 and the second reading circuit 4 can employ the existing detector reading circuit corresponding to the connected detector. The computing device 5 may be various devices for performing the computing function described in the present disclosure, comprising but not limited to a computer, a general purpose processor, a programmable logic controller (PLC), a digital signal processor (DSP), an application specific integrated circuit (ASIC), a field programmable gate array (FPGA), etc.

Figure 6:
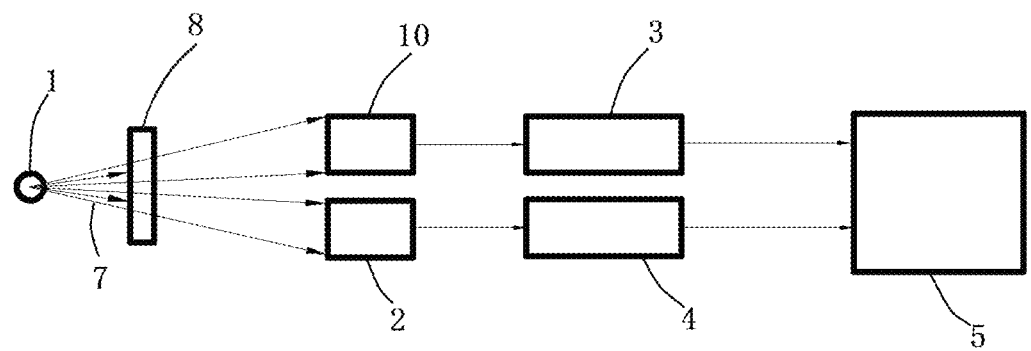
FIG. 6 is a principle diagram of an afterglow detection device according to another embodiment of the present disclosure.

FIG. 6 shows a principle diagram of an afterglow detection device of another embodiment of the present disclosure. As shown in FIG. 6, the difference between the embodiment of the present disclosure and the embodiment as shown in FIG. 4 lies in that the afterglow detection device further comprises a heavy metal sheet 8. The heavy metal sheet 8 is disposed on the beam-out side of the X-ray tube 1 and located between the X-ray tube 1 and the to-be-detected detector 10 and between the X-ray tube 1 and the residual ray detector 2, so as to attenuate the intensity of the X-ray beam.

Figure 7:
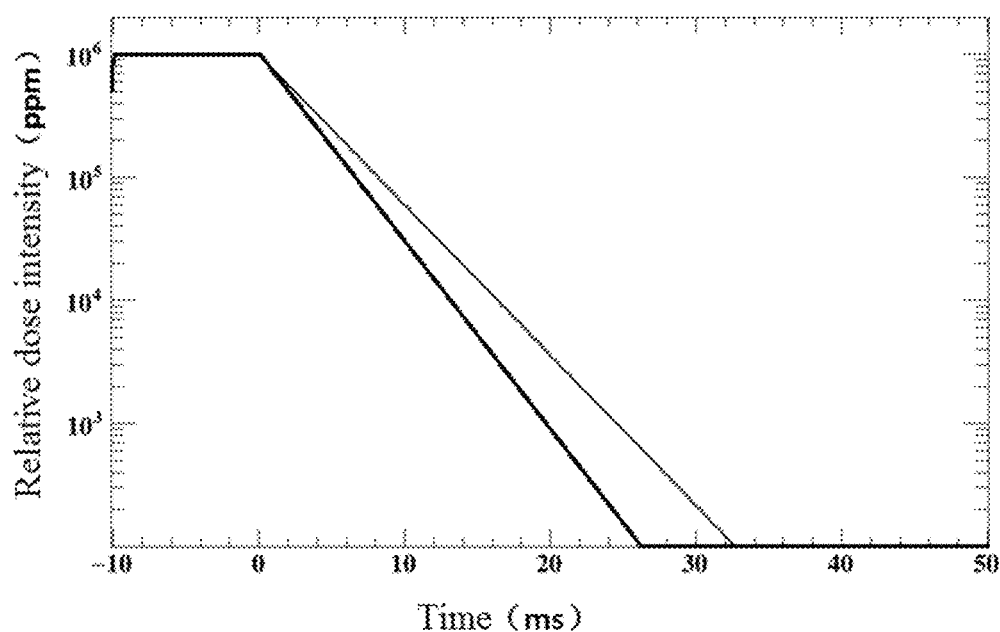
FIG. 7 is a comparison diagram of the output relative dose intensity curve of the residual ray detector (thin solid line) in the case that the heavy metal sheet is not disposed on the beam-out side of the X-ray tube and the output relative dose intensity curve of the residual ray detector (thick solid line) in the case that the heavy metal sheet is disposed.

FIG. 7 is a comparison diagram of the output relative dose intensity curve (thin solid line) of the residual ray detector in the case that the heavy metal sheet is not disposed on the beam-out side of the X-ray tube and the output relative dose intensity curve (thick solid line) of the residual ray detector in the case that the heavy metal sheet is disposed. In the figure, from −10 ms to 0 ms, the power supply for the X-ray tube 1 is turned on, and the X-ray tube 1 emits rays normally; after the moment of 0 ms, the power supply for the X-ray tube 1 is turned off, a residual X-ray beam is still emitted, and the dose intensity of the residual X-ray beam decreases with time. In this embodiment, the heavy metal sheet 8 is a steel plate, which is 4 mm thick and disposed on the beam-out side of the X-ray tube 1. As shown in FIG. 7, after the heavy metal sheet 8 is mounted, the intensity of the residual X-ray beam is attenuated more quickly.

The heavy metal sheet 8 is added on the beam-out side of the X-ray tube 1 and between the X-ray tube 1 and the to-be-detected detector 10 and between the X-ray tube 1 and the residual ray detector to relatively reduce the probability that low-energy X-ray photons in the X-ray beam arrive at the to-be-detected detector 10 and the residual ray detector 2, thereby relatively reducing the intensity of the residual X-ray beam arriving at the to-be-detected detector 10 and the residual ray detector 2, and the degree of attenuation of the residual X-ray beam is increased to reduce the effect of residual X-rays on the afterglow detection, thus being favorable for improving the accuracy of detection.

Finally, it should be noted that the above embodiments are merely used for illustrating the technical solutions of the present disclosure, instead of limiting the same. Although the present disclosure has been described in detail with reference to the preferred embodiments, it should be understood by the person of ordinary skill in the art that specific embodiments of the present disclosure can be modified or part of the technical features can be equivalently substituted. Those not departing from the technical solutions of the present disclosure should be encompassed in the scope of the technical solutions claimed by the present disclosure.

The invention claimed is:

1. An afterglow detection device, comprising:
   an X-ray tube for emitting an X-ray beam;
   a first reading circuit for receiving a first detected signal from a to-be-detected detector to form and output a first measurement signal according to the first detected signal, the to-be-detected detector being connected to the first reading circuit and disposed on a beam-out side of the X-ray tube to receive radiation of the X-ray beam and outputting the first detected signal to the first reading circuit at the time of detection;
   a residual ray detector disposed on a beam-out side of the X-ray tube;
   a second reading circuit connected to the residual ray detector for receiving a second detected signal from the residual ray detector to form and output a second measurement signal according to the second detected signal, the residual ray detector receiving radiation of the X-ray beam and outputting a second detected signal to the second reading circuit; and
   a computing device in signal connection with the first reading circuit and the second reading circuit to receive the first measurement signal and the second measurement signal, the computing device being configured to compute and output the afterglow detection signal according to the first measurement signal and the second measurement signal after a power supply for the X-ray tube is turned off.

2. The afterglow detection device according to claim 1, wherein
   the computing device is configured to subtract the value of the second measurement signal at a moment after the power supply for the X-ray tube is turned off from the value of the first measurement signal at that moment to serve as the value of the afterglow detection signal at that moment; or
   the computing device is configured to subtract a corrected value of the second measurement signal at a moment after the power supply for the X-ray tube is turned off from the value of the first measurement signal at that moment to serve as the value of the afterglow detection signal at that moment.

3. The afterglow detection device according to claim 1, wherein the output relative intensity of the residual ray detector at the moment of 10 ms after disappearance of an excitation signal is lower than 0.05% of the output relative intensity in the presence of the excitation signal.

4. The afterglow detection device according to claim 1, wherein the residual ray detector comprises a cadmium tungstate detector.

5. The afterglow detection device according to claim 1, wherein the afterglow detection device comprises a heavy metal sheet, the heavy metal sheet being disposed on the beam-out side of the X-ray tube and located between the X-ray tube and the to-be-detected detector and between the X-ray tube and the residual ray detector, so as to attenuate the intensity of the X-ray beam.

6. An afterglow detection method for detecting afterglow of a scintillation detector by using the afterglow detection device according to claim 1, comprising:
   turning on a power supply for the X-ray tube to emit an X-ray beam by the X-ray tube, and turning off the power supply for the X-ray tube after a period of time;
   receiving radiation of the X-ray beam and outputting a first detected signal by the to-be-detected detector;
   receiving the first detected signal, and forming and outputting a first measurement signal according to the first detected signal by the first reading circuit;
   receiving radiation of the X-ray beam and outputting a second detected signal by the residual ray detector;
   receiving the second detected signal, and forming and outputting a second measurement signal according to the second detected signal by the second reading circuit;
   receiving the first measurement signal and the second measurement signal, and computing and outputting an afterglow detection signal according to the first measurement signal and the second measurement signal by the computing device after the power supply for the X-ray tube is turned off.

7. The afterglow detection method according to claim 6, wherein
   the computing device subtracts the value of the second measurement signal at a moment after the power supply for the X-ray tube is turned off from the value of the first measurement signal at that moment to serve as the value of the afterglow detection signal at that moment; or
   the computing device subtracts the corrected value of the second measurement signal at a moment after the power supply for the X-ray tube is turned off from the value of the first measurement signal at that moment to serve as the value of the afterglow detection signal at that moment.

8. The afterglow detection method according to claim 6, wherein the first measurement signal is an output relative intensity of the to-be-detected detector, and the second measurement signal is an output relative intensity of the residual ray detector.

\* \* \* \* \*